(12) United States Patent
Wagner et al.

(10) Patent No.: US 9,827,139 B2
(45) Date of Patent: Nov. 28, 2017

(54) INTRAOCULAR LENS INJECTOR

(71) Applicant: Santen Pharmaceutical Co., Ltd., Osaka-shi (JP)

(72) Inventors: Christian Winfried Wagner, Osaka (JP); Yoshitaka Yamada, Osaka (JP); Katsuyuki Ueno, Osaka (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 25 days.

(21) Appl. No.: 14/437,577

(22) PCT Filed: Oct. 28, 2013

(86) PCT No.: PCT/JP2013/079079
§ 371 (c)(1),
(2) Date: Apr. 22, 2015

(87) PCT Pub. No.: WO2014/065426
PCT Pub. Date: May 1, 2014

(65) Prior Publication Data
US 2015/0272779 A1 Oct. 1, 2015

(30) Foreign Application Priority Data
Oct. 26, 2012 (JP) ................. 2012-237001

(51) Int. Cl.
*A61F 2/16* (2006.01)
*A61F 9/00* (2006.01)

(52) U.S. Cl.
CPC ............ *A61F 9/0017* (2013.01); *A61F 2/167* (2013.01); *F04C 2270/0421* (2013.01)

(58) Field of Classification Search
CPC ...... A61F 2/167; A61F 9/0017; A61F 2/1662; A61F 2/1664; A61F 2/1667;
(Continued)

(56) References Cited

U.S. PATENT DOCUMENTS

2004/0243141 A1 12/2004 Brown et al.
2005/0125000 A1 6/2005 Tourrette et al.
(Continued)

FOREIGN PATENT DOCUMENTS

EP 2072025 A1 6/2009
EP 2255751 A1 12/2010
(Continued)

*Primary Examiner* — Katrina Stransky
(74) *Attorney, Agent, or Firm* — The Webb Law Firm

(57) ABSTRACT

An intraocular lens injector includes a lens holder holding an intraocular lens which has an optic and a haptic extending in a curved shape from the optic, a plunger which comes into contact with the intraocular lens and pushes out the intraocular lens, and a device body in which the plunger is inserted projectably/retractably and in which the lens holder can be attached in an intersecting direction relative to an axis of the plunger. The lens holder includes a position regulating portion for regulating a disposing position of the haptic in such a manner that a distal end of the plunger at an initial position before the plunger is pushed in and the optic may be laid on a common plane with a portion of the haptic lying on top of the plunger.

3 Claims, 6 Drawing Sheets

(58) Field of Classification Search
CPC .... A61F 2/1672; A61F 2/1675; A61F 2/1678; A61F 2002/1681
USPC ...................................................... 623/6.12
See application file for complete search history.

(56) References Cited

U.S. PATENT DOCUMENTS

| | | |
|---|---|---|
| 2006/0200167 A1 | 9/2006 | Peterson et al. |
| 2007/0270881 A1 | 11/2007 | Hishinuma et al. |
| 2009/0171365 A1* | 7/2009 | Tanaka .................. A61F 2/1664 606/107 |
| 2010/0130985 A1 | 5/2010 | Tanaka |
| 2010/0286704 A1 | 11/2010 | Ichinohe et al. |
| 2011/0046635 A1 | 2/2011 | Pankin et al. |

FOREIGN PATENT DOCUMENTS

| | | |
|---|---|---|
| JP | 200441271 A | 2/2004 |
| JP | 200812016 A | 1/2008 |
| JP | 4648859 B2 | 12/2010 |
| JP | 2010273985 A | 12/2010 |
| JP | 20114979 A | 1/2011 |
| JP | 2011-45712 | 3/2011 |
| JP | 201145712 A | 3/2011 |
| JP | 4727497 B2 | 4/2011 |
| JP | 4727497 | 7/2011 |
| TW | 200425883 A | 12/2004 |
| WO | 03049645 A2 | 6/2003 |
| WO | 2007080869 A1 | 7/2007 |
| WO | WO 2007/080869 | 7/2007 |

\* cited by examiner

INTRAOCULAR LENS INJECTOR

CROSS-REFERENCE TO RELATED APPLICATIONS

This application is the United States national phase of International Application No. PCT/JP2013/079079 filed Oct. 28, 2013, and claims priority to Japanese Patent Application No. 2012-237001 filed Oct. 26, 2012, the disclosures of which are hereby incorporated in their entirety by reference.

TECHNICAL FIELD

The present invention relates to an intraocular lens injector including an extrinsic lens holder holding an intraocular lens which has an optic and a haptic extending in a curved shape from the optic, a plunger which comes into contact with the intraocular lens and pushes out this intraocular lens, and a device body in which the plunger is inserted projectably/retractably and in which the extrinsic lens holder can be attached in an intersecting direction relative to an axis of the plunger.

BACKGROUND ART

Conventionally, as one method of cataract surgery, there has been commonly implemented a method of treating by removing a clouded natural crystalline lens from the eye and then inserting an artificial intraocular lens into the eye. For the insertion of the intraocular lens into the eye, an insertion instrument called an injector is employed. This injector includes an instrument body having a placing portion on which the intraocular lens is to be placed and an inserting portion for guiding the intraocular lens into the eye, and a push-out member configured to come into contact with the intraocular lens with a distal end thereof for pushing out the lens (e.g. Patent Document 1).

The intraocular lens is pushed by the push-out member and then released into the eye while being progressively folded within the inserting portion. Therefore, the incision can be kept small for alleviating surgical load on the patient.

Patent Document 1 discloses an intraocular lens having a circular optical portion and a haptic extending in a curved shape from the optical portion. This intraocular lens is held by the instrument body. In this, a holding member is inserted from under the placing portion of the intraocular lens so as to place the intraocular lens upwardly of a push-out shaft and the distal end portion of the push-out member is placed under the intraocular lens. Under this condition, the product is shipped from a factory. Next, at the time of use of the injector, a user will pull out the holding member, whereby the haptic of the intraocular lens is placed on top of the distal end portion of the push-out member. With this arrangement, when the push-out member is pushed in, the distal end portion of this push-out member will not press the haptic, thus preventing deformation and damage of this haptic.

Further, the push-out member has a length which is set to allow the distal end of this push-out member to protrude sufficiently from the distal end of the insertion portion at the time of latter half stage in the inserting operation. With this arrangement, the intraocular lens can be released in a reliable manner from the distal end of the insertion portion to be eventually inserted into the eye.

CITATION LIST

Patent Literature

Patent Document 1: Japanese Unexamined Patent Application Publication No. 2010-273985 (FIG. 5, paragraphs [0016] and [0030]-[0036]).

SUMMARY OF INVENTION

Technical Problem

However, the conventional injector suffers following problems. The conventional injector is a so-called pre-loaded type which is shipped from a factor with an intraocular lens being set in advance in the instrument body. For this reason, in the course of transport or pulling-out of the holding member, there may occur displacement of the position of the distal end portion of the push-out member or the intraocular lens. Further, since the instrument body is kept under a sealed state, it is difficult for an operator to visually check such displacement in the position of the push-out member or the like. Moreover, in order to reset e.g. the push-out member to its proper position, the operator needs to disassemble the instrument body, so convenience is poor.

On the other hand, if the pushing-in of the plunger is started with the haptic being not placed on top of the push-out member appropriately, the distal end portion of the plunger will come into contact with the haptic inadvertently. As a result, the haptic may be deformed in an unexpected direction, thus collapsing or damaging its curved shape, whereby it becomes impossible to insert the intraocular lens to an appropriate position within the eye.

Further, with the pre-loaded type injector, due to mounting of an intraocular lens in the instrument in advance, it is necessary to keep the entire injector submerged in liquid, for proper storage of the intraocular lens in sterile distilled water until the lens is made available to a patient. This necessity causes enlargement of a storage container and gives discomfort to the operator at the time of use.

Further, since the distal end of the push-out member has a length that allows this distal end to protrude sufficiently from the distal end of the insertion portion, at the time of the latter half stage in the push-out operation, the operator carries out the operation while constantly watching so that the distal end portion of the push-out member will not come into contact with the intraocular tissue inadvertently. Generally, at the latter half stage of the push-out operation, the intraocular lens is inserted into the eye with progressive deformation of the lens, thus increasing contact force between the intraocular lens and the inner face of the insertion portion. Therefore, a larger force needs to be applied from the plunger for pushing out the intraocular lens. In this way, significant load will be imposed on the operator during the push-in operation of the plunger.

The present invention has been made in view of the above-described background art and the object of the invention is to provide an intraocular lens injector which is highly convenient and which can be manipulated in a reliable manner irrespective of an operator's skill.

Solution to Problem

An intraocular lens injector relating to this disclosure comprises:

an extrinsic lens holder holding an intraocular lens which has an optic and a haptic extending in a curved shape from the optic;

a plunger which comes into contact with the intraocular lens and pushes out the intraocular lens;

a device body in which the plunger is inserted projectably/retractably and in which the extrinsic lens holder can be attached in an intersecting direction relative to an axis of the plunger; and the extrinsic lens holder including a position regulating portion for regulating a disposing position of the haptic in such a manner that a distal end of the plunger at an initial position before the plunger is pushed in and the optic may be laid on a common plane with a portion of the haptic lying on top of the plunger.

With the above-described configuration, the extrinsic lens holder is attached to the device body in an intersecting direction relative to an axis of the plunger. And, the extrinsic lens holder includes a position regulating portion for regulating a disposing position of the haptic in such a manner that a distal end of the plunger before being pushed in and the optic may be laid on a common plane with a portion of the haptic lying on top of the plunger. As a result, only with an operation of assembling the extrinsic lens holder to the device body, the haptic will be placed on top of the distal end portion of the plunger. Therefore, when the plunger is pushed in, its distal end portion will not damage the haptic.

Further, when the intraocular lens is to be stored in sterile distilled water, it will suffice to store the extrinsic lens holder alone in a container. Thus, discomfort to the operator can be alleviated and convenience can be improved, in comparison with a situation of the entire injector being wetted in liquid.

Also, rather than the operation of assembling the extrinsic lens holder to the device body under the condition of the intraocular lens being set in the extrinsic lens holder in advance, the intraocular lens can be set in the extrinsic lens holder assembled to the device body with use of tweezers or the like. In this case, as the setting of the haptic is determined with reference to the position regulating portion of the extrinsic lens holder as a "mark", it is possible to place the haptic on the distal end of the plunger in a reliable manner.

With the above-described reliable placement of the haptic on top of the distal end portion of the plunger, damage of the haptic in association with push-in operation of the plunger can be avoided. As a result, it becomes possible to provide an intraocular lens injector which is highly convenient and which can be manipulated in a reliable manner irrespective of an operator's skill.

In the above-described configuration, preferably, in a bottom portion of the extrinsic lens holder, there is formed a cutout portion capable of introducing the distal end portion of the plunger located at the initial position before push-in operation to a position on the same plane as the optic.

In the case of the above-described arrangement of providing a cutout portion at a portion where the plunger is located, in order to allow the distal end portion of the plunger to be disposed on the same plane as the optic, it is possible to utilize the remaining portion, i.e. the portion devoid of such cutout portion for holding the optic and/or the haptic. For instance, it becomes possible for the portion other than the cutout portion to support the haptic of the intraocular lens. Then, when the extrinsic lens holder is assembled to the device body, the haptic can be placed on top of the distal end portion of the plunger in a reliable manner. In this way, with provision of a cutout portion in the bottom portion of the extrinsic lens holder, the haptic can be supported in a stable manner. Consequently, it becomes possible to provide an intraocular lens injector which is highly convenient and which can be manipulated in a reliable manner irrespective of the operator's skill.

In the above-described configuration, preferably, the position regulating portion comprises a protruding portion which protrudes from a bottom portion of the extrinsic lens holder into between the optic and the haptic.

With the above-described arrangement of providing a protruding portion as the position regulating portion between the optic and the haptic, it becomes possible to place the haptic on top of the distal end portion of the plunger in a reliable manner, with keeping the haptic away from the optic.

In the above-described configuration, preferably, the plunger includes a pushing portion applying a pushing force at its rear end and includes a stopper provided at a position different from the pushing portion and coming into contact with an end face of the device body opposite the extrinsic lens holder, thereby to prevent movement of the plunger in a push-in direction.

With the above-described configuration, it is possible for the stopper to prevent movement of the plunger by any amount more than needed.

Further, since the pushing-end position of the plunger can be confirmed by visually observing the stopper, there is no need for the operation with constantly confirming the position of the distal end portion of the plunger.

Therefore, the operation can be carried out with avoiding collision of the distal end portion of the plunger with the intraocular tissue. As a result, it becomes possible to provide an intraocular lens injector which is highly convenient and which can be manipulated in a reliable manner irrespective of the operator's skill.

In the above-described configuration, preferably, the device body includes a holding portion protruding to outside in an outer face of the end portion opposite the extrinsic lens holder, and the stopper sets a distance between the holding portion and the pushing portion to a predetermined distance.

Generally, when the intraocular lens is inserted into the eye with progressive deformation of the lens, the contact force between the intraocular lens and the inner face of the insertion portion is increased. Therefore, a larger force needs to be applied from the plunger for pushing out the intraocular lens. In this way, significant load will be imposed on the operator.

The operator will release the intraocular lens with hooking his/her index finger and middle finger on the holding portion of the device body and pressing the pushing portion of the plunger with his/her thumb.

With the above-described configuration, as the distance between the stopper and the pushing portion is set to such a distance which allows most effective pushing pressure at the timing of the latter half stage of the push-in operation, the pushing load to the operator can be alleviated. Incidentally, preferably, the predetermined distance is set to range from 10 to 50 mm, which range allows a human having standard sized hands can push-in the plunger with using the second joint of the index finger and the middle finger as "pivots".

DESCRIPTION OF EMBODIMENTS

Next, embodiments of an intraocular lens injector 1 relating to this disclosure will be explained with reference to the accompanying drawings. It should be noted however that the present invention is not limited to these embodiments, but can be modified in various ways as long as such modifications do not deviate from the essence thereof.

1. General Configuration

Figure 1:
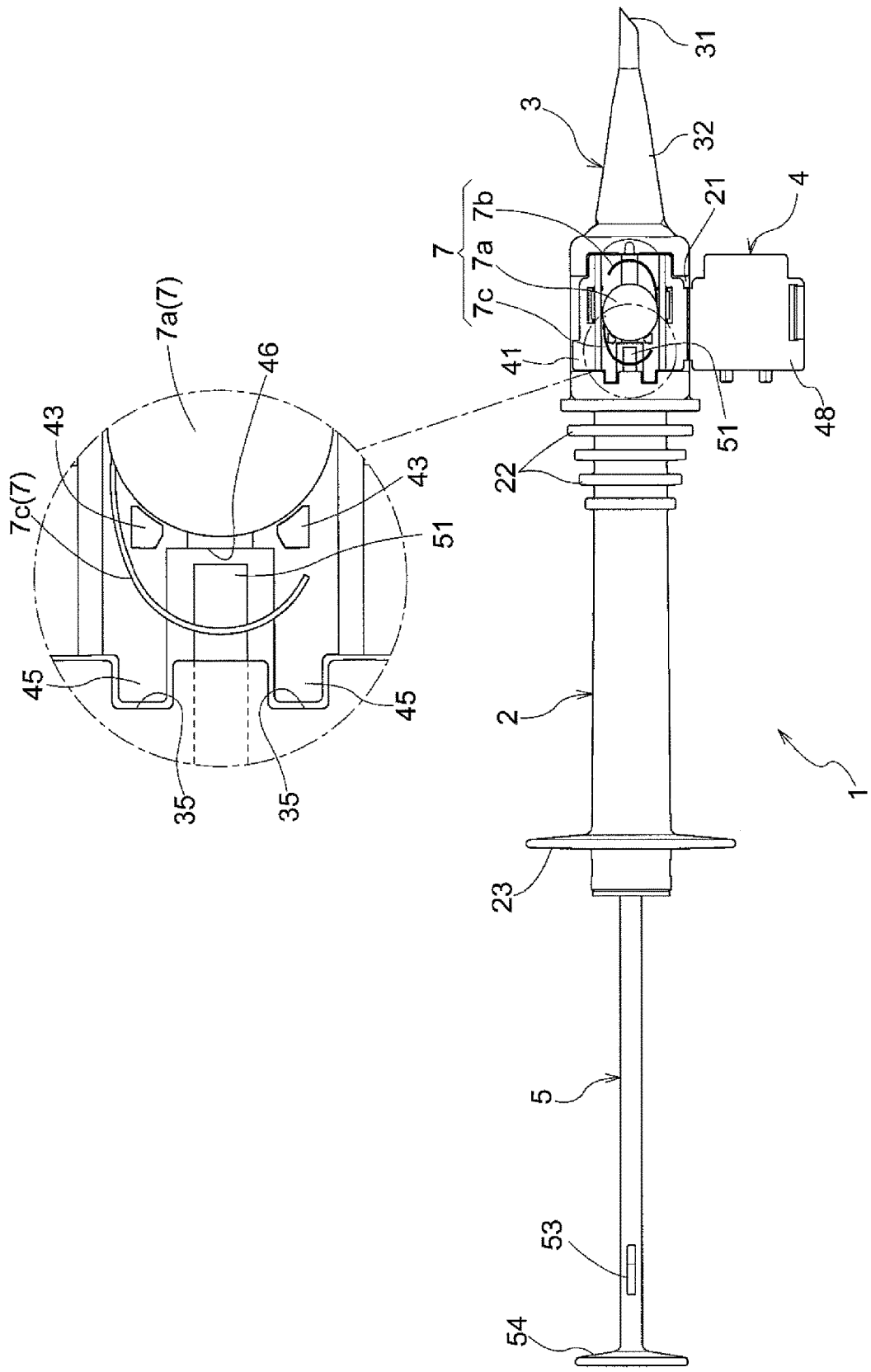
FIG. 1 is an overall view of an intraocular lens injector.

FIG. 1 shows an overall view of an intraocular lens injector 1 ("injector 1" hereinafter) according to this embodiment. This injector 1 includes a cylindrical device body 2, a distal end tip 3 connected to the device body 2, an extrinsic lens holder 4 that can be attached to the device body 2, and a bar-like plunger 5 inserted in the device body 2. An intraocular lens 7 includes an optic 7a as a substitute implant for a natural crystalline lens, and a pair of front and rear haptics 7b and 7c extending in a curved shape from the optic 7a and this intraocular lens 7 is held in the extrinsic lens holder 4. Incidentally in the instant embodiment, there is shown one example of such intraocular lens 7 of a three-piece type, having the optic 7a and the pair of haptics 7b, 7c.

In the following discussion, explanation will be given with referring the axial direction of the plunger 5 as a front/rear direction, the directions perpendicular to the axis as the upper/lower, right/left directions.

2. Device Body

The device body 2 includes a receiving portion 21 provided on the front side thereof for allowing engagement thereto of the distal end tip 3 and the extrinsic lens holder 4, a plurality of annular protruding portions 22 provided in an outer face at the front end thereof to be gripped by an operator, and a flange-like holding portion 23 provided in the outer face at the rear end to be held by the operator by hooking his/her fingers thereon. The device body 2 is formed with using a resin having shock resistance such as polycarbonate.

Incidentally, the annular protruding portions 22 and the holding portion 23 can be shaped in any way as long as the requisite functions thereof can be achieved. For instance, the holding portion 23 can be formed like a projection that allows finger hooking, rather than the flange-like shape.

In operation, the operator will push-in the plunger 5 by one hand and will rotate the annular protruding portions 22 by the other hand, thereby to release the intraocular lens 7 into a patient's eye in the order of succession of the front haptic 7b, the optic 7a and then the rear haptic 7c. The provision of the annular protruding portions 22 facilitates the operator's gripping of the injector 1, thus providing improvement of the maneuverability of the injector 1.

3. Distal End Tip

Figure 2:
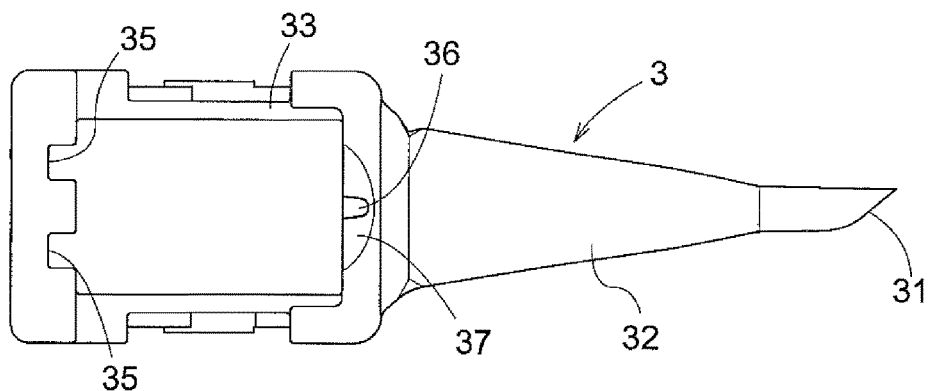
FIG. 2 is a plan view of a distal end tip.
Figure 3:
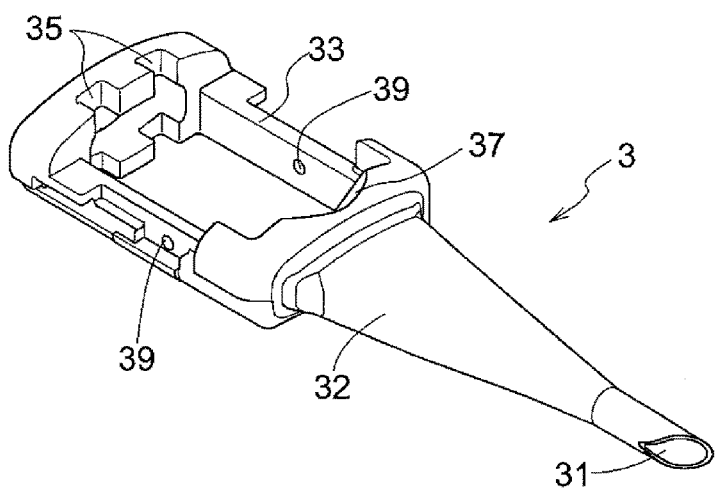
FIG. 3 is a perspective view of the distal end tip.

FIG. 2 and FIG. 3 show a plane view and a perspective view of the distal end tip 3. The distal end tip 3 includes a releasing portion 31 for releasing the intraocular lens 7, a tapered portion 32 having an inner diameter which increases progressively toward the rear side, and a rectangular portion 33 having an aperture at the center thereof and having a rectangular outer circumference. As the rectangular portion 33 is engaged with the receiving portion 21 of the device body 2, the distal end tip 3 is connected to the device body 2. Incidentally the mode of engagement between the distal end tip 3 and the device body 2 can vary in any desired manner, such as engagement between a retaining pawl and a retaining hole, for instance. The distal end tip 3 is formed with using a resin having chemical resistance and softness, such as polyamide.

The intraocular lens 7 will be pushed by the plunger 5 and progressively folded as it is passed in the inside of the tapered portion 32. Then, the intraocular lens 7 under a condition of opposed ends of the optic 7a being folded, will reach the releasing portion 31. After the intraocular lens 7 reaches the releasing portion 31, firstly, the front haptic 7b will enter the eye and then the optic 7a will enter the eye from the cut side of the releasing portion 31. Lastly, the rear haptic 7c with keeping its curved shape will enter the eye, whereby the optic 7a is supported.

The rectangular portion 33 includes rear recess portions 35 engageable with rear protrusions 45 of the extrinsic lens holder 4 and engaging hole portions 39 engageable with retaining pawls 49 of the extrinsic lens holder 4. The rectangular portion 33 includes also, on the front side thereof, an injection hole portion 36 through which an amount of elasto-viscous substance such as hyaluronate sodium can be injected with use of a syringe and an injection recess portion 37 formed around the injection hole portion 36.

At the time of use of the injector 1, the extrinsic lens holder 4 will be inserted into the aperture of the rectangular portion 33. In this, as the front and rear portions of the rectangular portion 33 of the distal end tip 3 are formed asymmetric, the operator can carry out the inserting operation without erring in the setting direction of the extrinsic lens holder 4. Further, when a needle of the syringe is inserted into the injection hole portion 36, the distal end of this syringe needle is guided by the injection recess portion 37. Therefore, the injection of the elasto-viscous substance can proceed in a reliable manner.

4. Plunger

Figure 4:
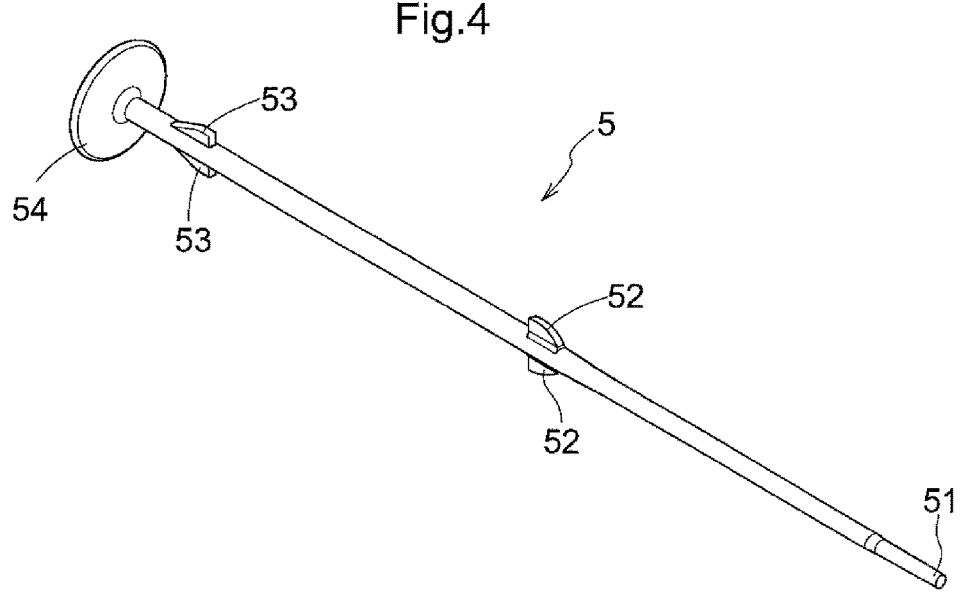
FIG. 4 is a perspective view of a plunger.

FIG. 4 shows a perspective view of the plunger 5. The plunger 5 includes a distal end portion 51 having a flat face for coming into contact with the optic 7a of the intraocular lens 7, retaining portions 52 to be retained by the rear end of the device body 2, stoppers 53 formed at the rear side and protruding to the outside, and a flange-like pushing portion 54 provided rearwardly of the stoppers 53. The plunger 5 is formed with using a resin having shock resistance such as polycarbonate.

Incidentally, the shapes of the distal end portion 51, the stoppers 53 and the pushing portion 54 can vary in any way as long as the requisite functions thereof can be achieved. For instance, in the face of the distal end portion 51 which face comes into contact with the optic 7a, a projection for clamping the optic 7a can be provided.

The plunger 5 will be inserted into the device body 2 from the rear side thereof, and as the retaining portions 52 come to be retained by the rear end of the device body 2, the plunger 5 will be set at its initial position prior to a push-in operation where the distal end portion 51 will be located within a cutout portion 46 of the extrinsic lens holder 4.

Further, an arrangement is provided such that in the course of push-in of the plunger 5, with advancing of the intraocular lens 7 in the inside of the tapered portion 32 of the distal end tip 3, a contact force between the inner surface of the distal end tip 3 and the optic 7a will increase progressively. As this arrangement causes progressive reduction in the advancing speed of the plunger 5, uncontrolled sudden release of the intraocular lens 7 can be prevented. Incidentally as an alternative, an elastic element (not shown) such as a spring can be provided along the outer circumference face of the plunger 5 on its side closer to the distal end portion 51 than the retaining portions 52 and the inner circumference face of the device body 2. With this arrangement, the push-in operation of the plunger 5 will encounter a reaction force from the elastic element, so that uncontrolled sudden release of the intraocular lens 7 from the distal end portion 51 of the plunger 5 can be prevented. The disposing position of such elastic element is not particularly limited. For instance, the element can be disposed also between the pushing portion 54 of the plunger 5 and the rear end of the device body 2. Any other arrangement will be possible as long as the push-in operation of the plunger 5 will encounter a reaction force from the elastic element.

Figure 10:
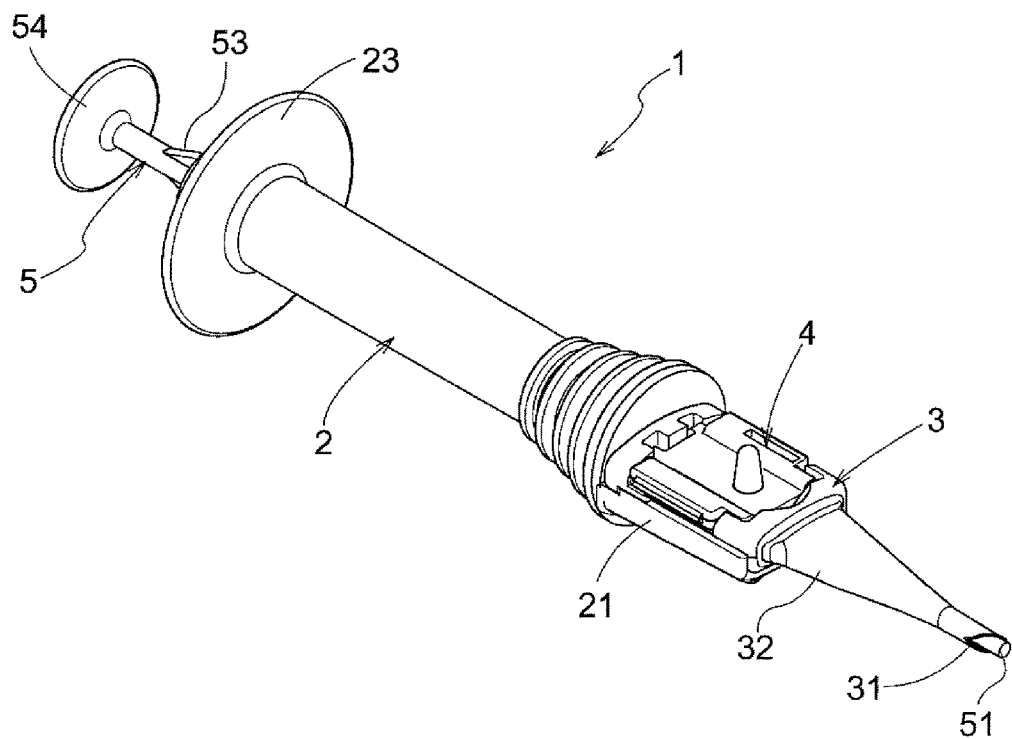
FIG. 10 is a schematic diagram showing a pushing-end position.

On the other hand, upon release of the intraocular lens 7 to the outside, the elastic force of this intraocular lens 7 is released, which force would promote quickened advancing of the plunger 5 to the front side. However, in the instant embodiment, the stoppers 53 are configured to protrude largely so as to be stopped at the rear end of the device body 2, so that as shown in FIG. 10, the movement of the plunger 5 is stopped at a push-in completion position. For this reason, no adjusting in the pushing force is required from the operator and accidental contact of the distal end portion 51 with the intraocular tissue due to sudden uncontrolled advancement of the plunger 5 upon release of the elastic force of the intraocular lens 7 can be prevented in a reliable manner. Moreover, it is also possible to visually confirm the push-in completion position by viewing the stoppers 53. So, there is no need for the operator to carry out the operation while constantly checking the position of the distal end portion 51 of the plunger 5.

The stoppers 53 are configured to set the distance between the holding portion 23 of the device body 2 and the pushing portion 54 of the plunger 5 to a predetermined distance to be described next. Namely, in the course of insertion of the intraocular lens 7 into the eye, the contact force between the inner face of the distal end tip 3 and the optic 7a increases progressively. So, a relatively large pushing force is required at the latter half stage of the push-in operation. Further, the intraocular lens 7 is gradually inserted into the eye in association with progressive deformations of the front haptic 7b, the optic 7a and the rear haptic 7c one after another in this mentioned order. This also contributes to progressive increase in the required pushing force of the plunger 5. Namely, the pressing load on the operator will be at its maximum when the intraocular lens 7 is about to be released.

For instance, the operator will hook his/her index finger and middle finger on the holding portion 23 of the device body 2 and press the pushing portion 54 of the plunger 5 by his/her thumb to release the intraocular lens 7. In this, the pressing burden on the operator can be alleviated by an arrangement of setting the distance between the holding portion 23 of the device body 2 and the pushing portion 54 of the plunger 5 to the predetermined distance that allows most effective exertion of the pressing force by the operator.

The distance over which a person having standard sized hands can carry out a push-in operation of the plunger 5 with using the second joint between the index finger and the middle finger as the pivot ranges from 0 to 100 mm. For this reason, it is preferred that the distance between the holding portion 23 and the pushing portion 54 when the push-in operation of the plunger 5 is completed range from 10 to 50 mm. Further, if the distance between the holding portion 23 and the pushing portion 54 when the push-in operation of the plunger 5 is completed is set from 10 mm to 30 mm, this will allow most effective exertion of pressing force at the time of the release of the intraocular lens 7 which time requires very careful manipulation of the plunger 5.

5. Extrinsic Lens Holder

Figure 5:
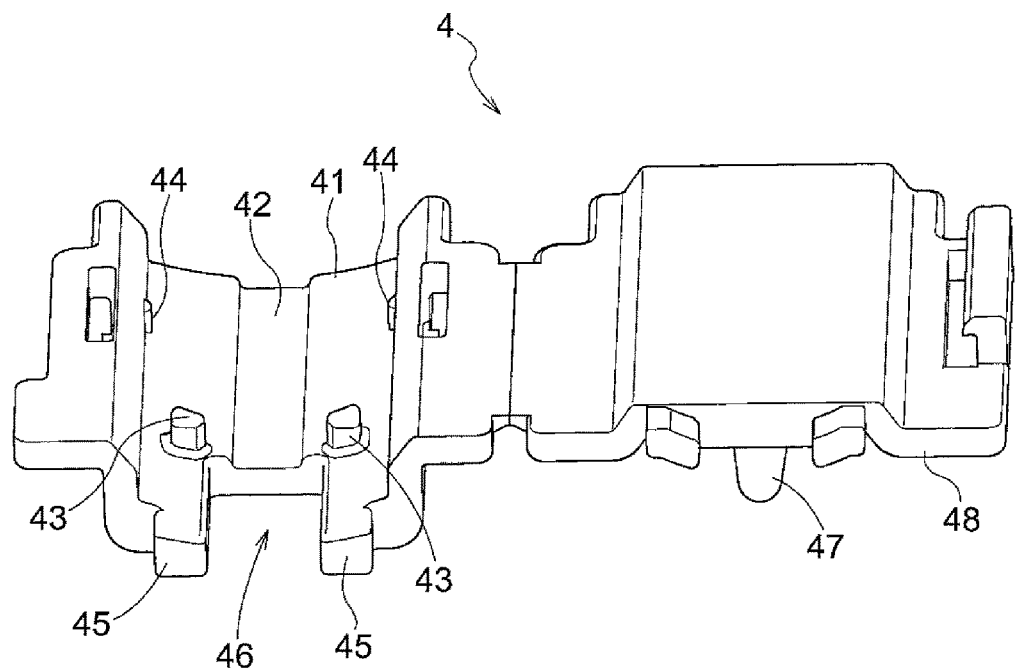
FIG. 5 is a perspective view of an extrinsic lens holder under an opened state.
Figure 6:
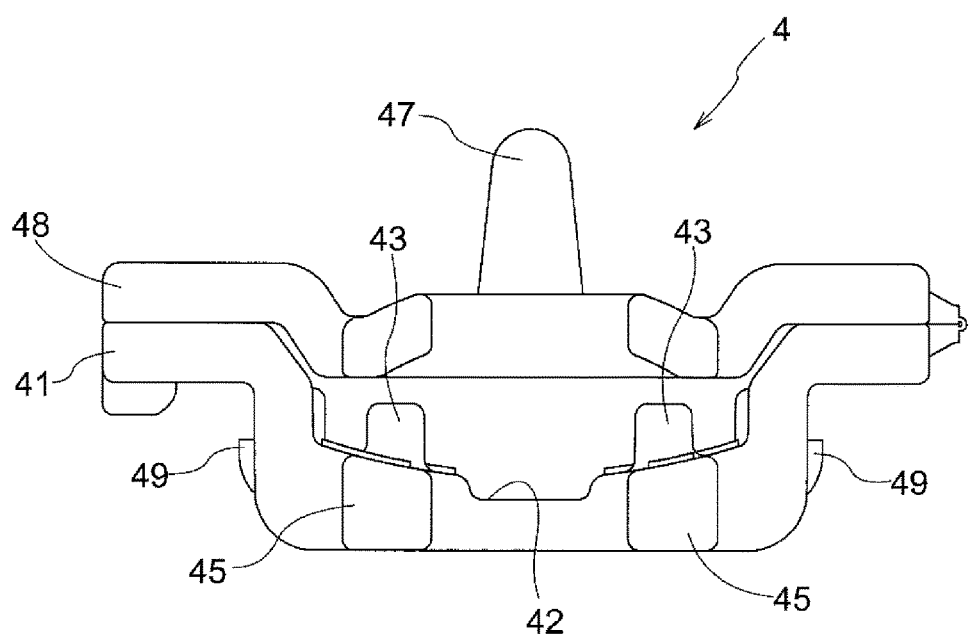
FIG. 6 is a perspective view of the extrinsic lens holder under a closed state.

FIG. 5 and FIG. 6 show a perspective view and a side view of the extrinsic lens holder 4. The extrinsic lens holder 4 includes a bottom portion 41 on which the intraocular lens 7 is to be placed, and a lid portion 48 connected to the bottom portion 41 and openable/closable. After placement of the intraocular lens 7 on the bottom portion 41, the lid portion 48 is closed, thus holding the intraocular lens 7. The extrinsic lens holder 4 is formed of using a resin having chemical resistance such as polypropylene.

The bottom portion 41 of the extrinsic lens holder 4 includes a groove portion 42 formed at the center thereof and extending along the front/rear direction, a pair of protruding portions 43 (an example of "a position regulating portion") formed rearwardly and on right and left sides of the groove portion 42, side protrusions 44 protruding from the lateral sides, rear protrusions 45 engageable with the rear recess portions 35 of the extrinsic lens holder 4 and the cutout portion 46 formed by cutting out the center of the rear end. Further, on the outer face of the extrinsic lens holder 4 in opposition to the bottom portion 41, there are provided the retaining pawls 49 engageable with the engaging hole portions 39 of the distal end tip 3. Incidentally, instead of providing the engaging hole portions 39 in the distal end tip 3, it is also possible to cause the retaining pawls 49 of the extrinsic lens holder 4 to be engaged with the receiving portion 21 of the device body 2.

Further, the shapes of the protruding portions 43 and the cutout portion 46 can vary in any way as long as the requisite functions thereof can be achieved. For instance, it can be a shape having a cutout portion 46 which is opened entirely on the rear side from the protruding portion 43.

The protruding portions 43 are disposed between the optic 7a and the rear haptic 7c of the intraocular lens 7, so that the intraocular lens 7 is held in the extrinsic lens holder 4 with keeping the rear haptic 7c away from the optic 7a. At that time, as shown in FIG. 1, the rear haptic 7c traverses the cutout portion 46 having a cutout at the center of the rear end. Further, as the front haptic 7b abuts the side protrusions 44, rotation of the intraocular lens 7 is restricted. In this way, by the protruding portions 43 and the side protrusions 44, the intraocular lens 7 is maintained at a fixed position in the extrinsic lens holder 4. Therefore, displacement in the position of the intraocular lens 7 will hardly occur, at the time of transport of the injector 1 or by some unexpected external force.

Incidentally, it will be advantageous to provide the contacting face of the protruding portion 43 to come into contact with the optic 7a with a same curvature as the curvature of the circumferential edge of the optic 7a. With this arrangement, it becomes possible for the optic 7a and the protruding portion 43 to come into contact by a predetermined distance along the circumferential direction of the optic 7a. Consequently, even more stable holding is made possible.

With the above-described mode of holding with the rear haptic 7c traversing the cutout portion 46, when the extrinsic lens holder 4 is to be assembled to the device body 2 from the upper side thereof, the rear haptic 7c will lie on top of the distal end portion 51 of the plunger 5. That is, thanks to the cutout portion 46, the distal end portion 51 of the plunger 5 located at its initial pre-pushing position will be introduced to and received at the position in the same plane as the intraocular lens 7.

Further, it becomes also possible to support the rear haptic 7c with the other portion than the cutout portion 46. Consequently, when the extrinsic lens holder 4 is assembled to the device body 2, it is possible to place the rear haptic 7c on top of the distal end of the plunger 5 in a reliable manner. In this way, with provision of the cutout portion 46 in the bottom portion 41 of the extrinsic lens holder 4, stable support of the rear haptic 7c is made possible.

Further, when the extrinsic lens holder 4 is to be assembled to the device body 2 from the upper side thereof, as the protruding portions 43 keep the rear haptic 7c away from the optic 7a, the rear haptic 7c can be reliably placed on top of the plunger 5.

Therefore, it is possible to avoid e.g. deformation of the rear haptic 7c in an unexpected direction and resultant break thereof which may occur by accidental contact to the distal end portion 51 of the plunger 5 by the protruding portions 43 at the time of start of push-in operation of the plunger 5.

After completion of initial setting of the injector 1, the distal end portion 51 of the plunger 5 will be pushed in along the groove portion 42 while being kept in contact with the optic 7a. With this, the rear haptic 7c lying on top of the plunger 5 will pass the protruding portions 43 and will smoothly advance with keeping its curved shape. In this, the advancing direction of the plunger 5 will be kept fixed by the groove portion 42.

Further, in the outer face of the lid portion 48, there is formed a grip portion 47 projecting therefrom to the outside. When the lid portion 48 of the extrinsic lens holder 4 is opened/closed in order to mount the intraocular lens 7, the opening/closing operation is possible with gripping the grip portion 47. Thus, operational ease is provided.

Figure 7:
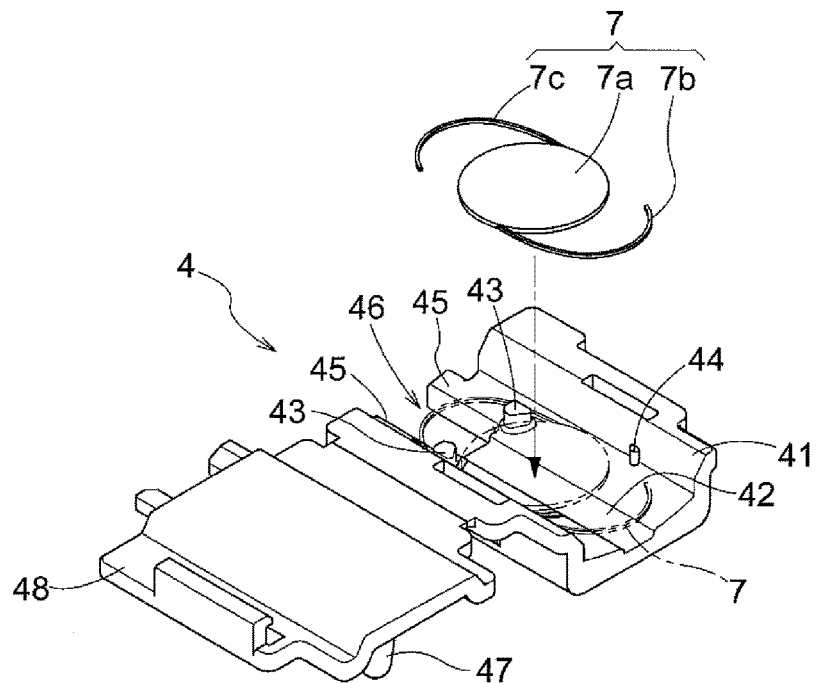
FIG. 7 is a schematic diagram illustrating an assembly procedure.

Incidentally, the intraocular lens 7 can be set in the injector 1 in which the extrinsic lens holder 4 is set in the device body 2 in advance and the grip portion 47 can be omitted. In the above case of setting the intraocular lens 7 in the extrinsic lens holder 4 set in the device body 2 in advance, the intraocular lens 7 can be set in the extrinsic lens holder 4 with use of tweezers or the like so that the protruding portions 43 may be disposed between the optic 7a and the rear haptic 7c as shown in FIG. 7. Thus, good convenience is provided.

6. Assembly Procedure

Figure 8:
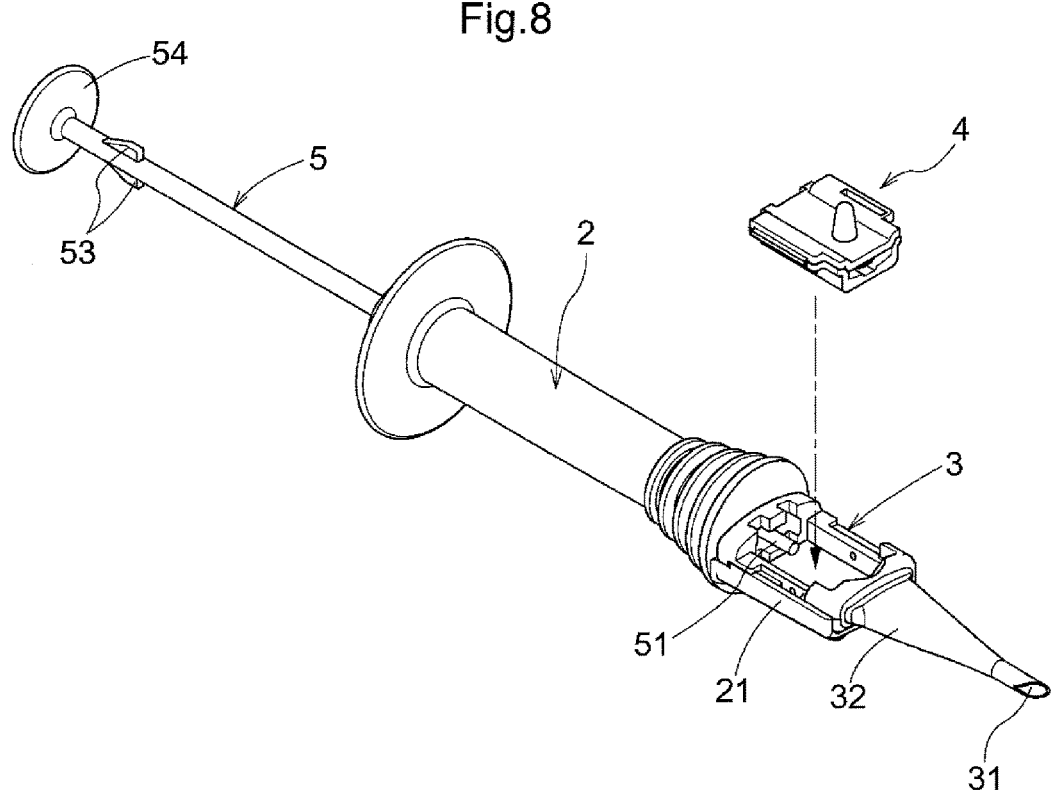
FIG. 8 is a schematic diagram illustrating the assembly procedure.
Figure 9:
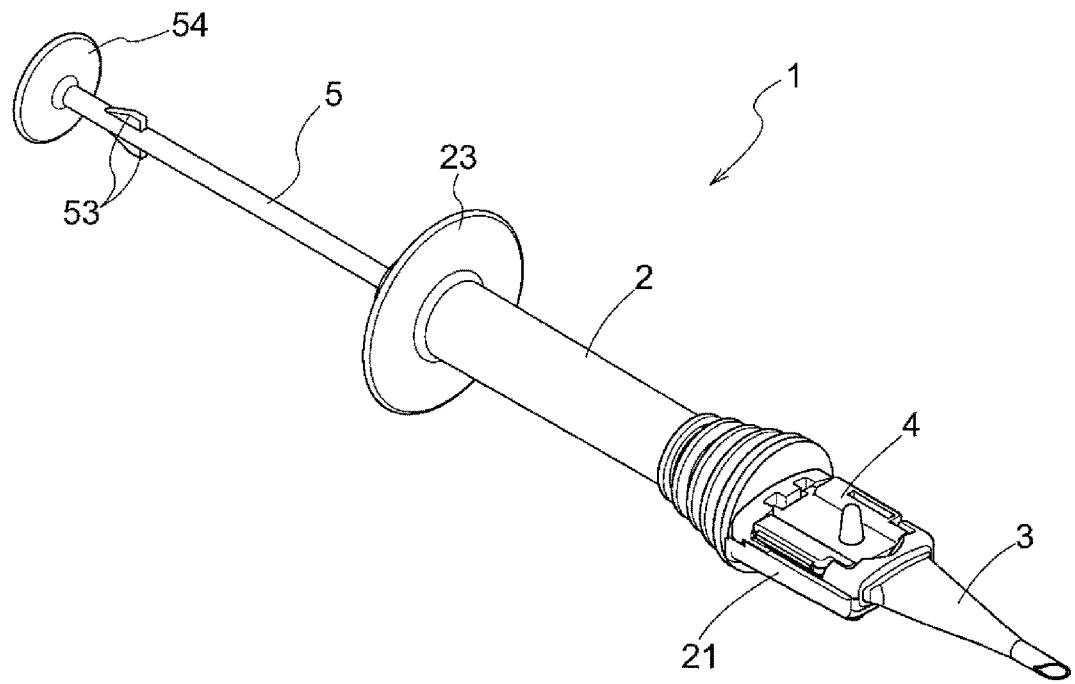
FIG. 9 is a schematic diagram illustrating the assembly procedure.

With reference to FIGS. 7 through 9, an assembly procedure of the injector 1 will be explained.

First, the distal end tip 3 is inserted and engaged to/with the device body 2 from the upper side thereof. Next, the plunger 5 is inserted into the device body 2 from the rear end thereof. In this, as shown in FIG. 8, as the retaining portions 52 of the plunger 5 are retained and stopped by the rear end of the device body 2, the plunger 5 will be fixed in position such that the distal end portion 51 of the plunger 5 may enter the cutout portion 46 of the extrinsic lens holder 4. Therefore, possibility of displacement of the plunger 5 and the distal end tip 3 from the device body 2 during transport is lessened.

Next, with reference to FIG. 7, the extrinsic lens holder 4 will be explained. Firstly, the intraocular lens 7 is placed on the bottom portion 41 of the extrinsic lens holder 4. This placing operation will be effected such that the rear face of the optic 7a to be directed to a patient's eye faces downwards and the circumferential edge portion of the optic 7a may come into contact with the protruding portions 43. With this, the rear haptic 7c will be placed on the rear side across the protruding portions 43 to extend over across the cutout portion 46. Simultaneously, the front haptic 7b will come into contact with the side protrusions 44, whereby the ocular lens 7 will be held at the predetermined position in the extrinsic lens holder 4. Under this condition, the lid portion 48 will be closed and then the holder will be introduced into an unillustrated holder storage container containing sterile distilled water and kept under a sealed state. In this, as the intraocular lens 7 is regulated in its movement by means of the protrusions 43 and the side protrusions 44, positional displacement thereof during transport is effectively lessened.

Also, as only the extrinsic lens holder 4 needs to be stored in the container containing sterile distilled water, the operator will feel less psychological resistance in touching the container wetted with liquid than a case of storage with the intraocular lens 7 being set in advance inside the injector 1.

Next, with reference to FIG. 8, a method of setting the injector 1 by an operator will be explained. Firstly, the operator will remove the device body 2 or the like assembled in a factory from the unillustrated container. In doing this, the operator will visually confirm the distal end portion 51 of the plunger 5 protruding from the front end of the device body 2. As the front side of the device body 2 is opened upwards, the operator can easily confirm the position of the distal end portion 51 of the plunger 5 located at its initial pre-push-in position.

Next, the operator will remove the extrinsic lens holder 4 from the unillustrated storage container and then assemble the holder 4 with the device body 2 from the upper side, that is, along a direction intersecting the axial direction of the plunger 5. With this, the rear haptic 7c of the intraocular lens 7 will be placed on top of the distal end portion 51 of the plunger 5 in a reliable manner. Therefore, assembly can be carried out easily, irrespective of the operator's skill. Subsequently, an amount of elasto-viscous substance will be injected via the injection hole portion 36 of the distal end tip 3. With this, the plunger 5 will be set to its initial state from which it can be pushed in as shown in FIG. 9.

In the case of setting the intraocular lens 7 in the extrinsic lens holder 4 set in the device body 2, firstly, from above the device body 2, that is, along a direction intersecting the axial direction of the plunger 5, the extrinsic lens holder 4 will be assembled to the device body 2. This assembly can be carried out at the time of assembly at the factory or at the time of use. At the time of use, the operator will visually confirm the distal end portion 51 of the plunger 5 protruding from the front end of the device body 2. Then, the operator will remove the intraocular lens 7 from an unillustrated lens storage container and set it in the extrinsic lens holder 4 with use of e.g. tweezers such that the protruding portions 43 may be disposed between the optic 7a and the rear haptic 7c. With this, the rear support portion 7c of the intraocular lens 7 will be placed on top of the distal end portion 51 of the plunger 5 in a reliable manner. Thus, high convenience is provided. Then, as an amount of elasto-viscous substance is injected via the injection hole portion 36 of the distal end tip 3, the plunger 5 will be set to its initial state from which it can be pushed in as shown in FIG. 9.

7. Operational Procedure

FIG. 10 is a diagram showing the push-in completion position.

After setting of the injector 1 at the initial position as shown in FIG. 9, the operator will start a push-in operation of the plunger 5. In this, the operator will push in the plunger 5 at a position away from the patient so that the releasing portion 31 of the distal end tip 3 will not come into contact with the intraocular tissue. Next, after confirming the push-in situation of the plunger 5 with visual checking of the stoppers 53 of the plunger 5, at a point when the push-in operation has progressed to a certain extent, the operator will insert the releasing portion 31 into the patient's eye. Then, under the condition immediately before exit of the distal end portion 51 of the plunger 5 from the releasing portion 31 illustrated in FIG. 10, the operator will slowly rotate the injector 1 and release the intraocular lens 7 into the eye with orienting the cut side of the releasing portion 31 toward the far side of the eye.

Figure 11:
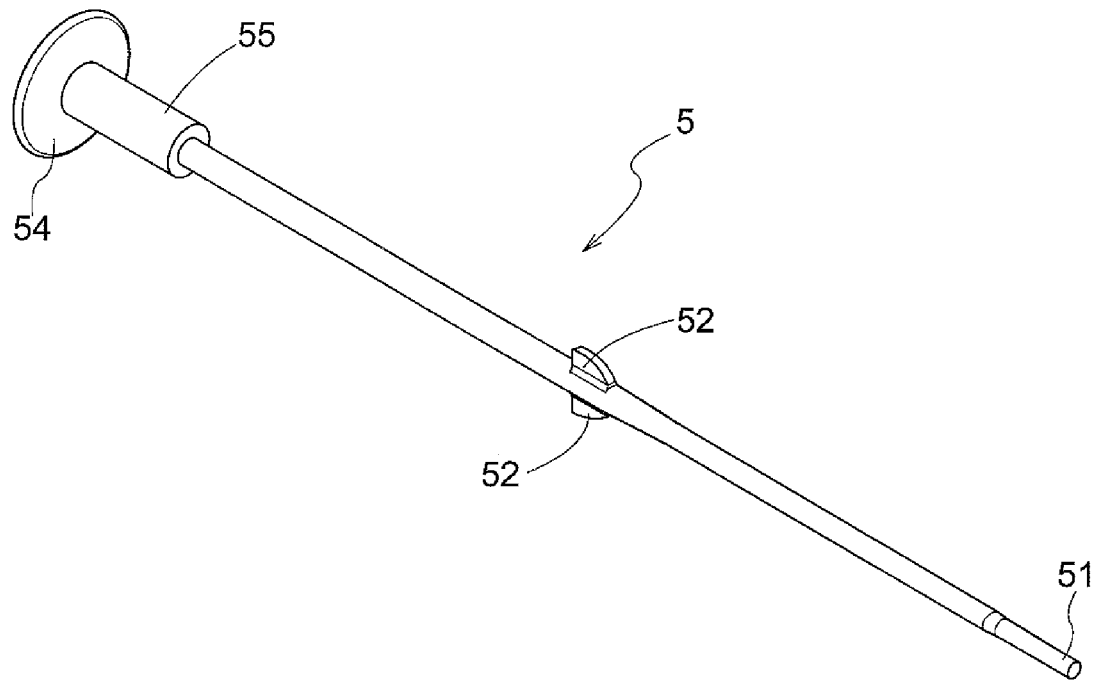
FIG. 11 is a perspective view showing a plunger according to a further embodiment.

Other Embodiments (1) As shown in FIG. 11, the plunger 55 of the plunger 5 can have a cylindrical shape which extends continuously to the pushing portion 54. With this, the rigidity of the plunger 5 at its portion relating to the above cylindrical shape will be increased, so that deformation thereof due to a strong pressure in the push-in direction will be restricted. Consequently, the push-in operation of the intraocular lens 7 will be more stable.

(2) Alternatively various modifications will be possible as long as prevention of advance of the plunger 5 is ensured, such as providing the stopper 55 of the plunger 5 with a flange-like shape or a flat shape, etc.

(3) As the position regulating portion of the extrinsic lens holder 4, in the upper face of the protruding portion 43, there can be provided a recess capable of accommodating the rear haptic 7c of the intraocular lens 7. With this, the stability of the rear haptic 7c can be enhanced. Consequently, during transport of the injector 1, inadvertent movement of the intraocular lens 7 can be restricted even more effectively.

(4) Further alternatively, various modifications of the position regulating portion of the extrinsic lens holder 4 will be possible as long as the rear haptic 7c may be caused to traverse the cutout portion 46 and such modified arrangements are suitable for storage of the intraocular lens 7.

(5) In the foregoing, regulation of movement of the intraocular lens 7 for the purpose of prevention of positional displacement during transport or the like is realized by establishment of contact between the side protrusions 44 provided in the extrinsic lens holder 4 and the front haptic 7b of the intraocular lens 7. However, the side protrusions 44 can be omitted. In this case too, since the protruding portions 43 are disposed between the rear haptic 7c and the optic 7a, movement of the intraocular lens can still be regulated.

Figure 12:
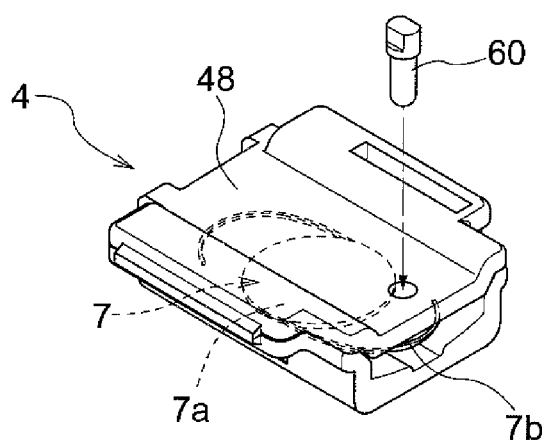
FIG. 12 is a perspective view showing an extrinsic lens holder in the further embodiment.

(6) As shown in FIG. 12, a hole can be provided at a front portion of the lid portion 48 of the extrinsic lens holder 4 and a regulating pin 60 can be inserted into this hole. As a result, the regulating pin 60 is disposed between the front haptic 7b and the optic 7a of the intraocular lens 7 held in the extrinsic lens holder 4, thus, inadvertent movement of the intraocular lens 7 can be restricted. In this case, the push-in operation of the plunger 5 will be carried out after removal of the regulating pin 60. Thus, with the push-in operation of the plunger 5, the intraocular lens 7 can be advanced smoothly.

INDUSTRIAL APPLICABILITY

The present invention is applicable to an intraocular lens injector for use in inserting an intraocular lens into an eye.

REFERENCE SIGNS LIST

1: intraocular lens injector
2: device body
23: holding portion
4: extrinsic lens holder
41: bottom portion
43: protruding portion (position regulating portion)
46: cutout portion
5: plunger
51: distal end portion
53: stopper
54: pushing portion
7: intraocular lens
7a: optic
7b: front haptic (haptic)
7c: rear haptic (haptic)

The invention claimed is:

1. An intraocular lens injector comprising:
an extrinsic lens holder holding an intraocular lens which has an optic and a haptic extending in a curved shape from the optic;
a plunger which comes into contact with the intraocular lens and pushes out the intraocular lens;
a device body in which the plunger is inserted projectably/retractably and in which the extrinsic lens holder can be attached in an intersecting direction relative to an axis of the plunger;
the extrinsic lens holder including a position regulating portion for regulating a disposing position of the haptic in such a manner that a distal end of the plunger at an initial position before the plunger is pushed in and the optic may be laid on a common plane with a portion of the haptic lying on top of the plunger; and
wherein in a bottom portion of the extrinsic lens holder, there is formed a cutout portion capable of introducing the distal end portion of the plunger located at the initial position before push-in operation to a position on the same plane as the optic; and wherein the position regulating portion comprises a protruding portion which protrudes from the bottom portion of the extrinsic lens holder between the optic and the haptic.

2. The intraocular lens injector according to claim 1, wherein the plunger includes a pushing portion applying a pushing force at its rear end and includes a stopper provided at a position different from the pushing portion and coming into contact with an end face of the device body opposite the extrinsic lens holder, thereby to prevent movement of the plunger in a push-in direction.

3. The intraocular lens injector according to claim 2, wherein the device body includes a holding portion protruding to outside on an outer face of the end portion opposite the extrinsic lens holder, and
the stopper sets a distance between the holding portion and the pushing portion to a predetermined distance.

* * * * *